United States Patent [19]

Suzuki

[11] Patent Number: 5,644,375
[45] Date of Patent: Jul. 1, 1997

[54] OPHTHALMIC APPARATUS PROVIDED WITH ALIGNMENT MECHANISM PRELIMINARY CLASS

[75] Inventor: Nobuo Suzuki, Nukata-gun, Japan

[73] Assignee: Nidek Co., Ltd., Japan

[21] Appl. No.: 529,402

[22] Filed: Sep. 18, 1995

[30] Foreign Application Priority Data

Sep. 30, 1994 [JP] Japan ................... 6-260980
Sep. 30, 1994 [JP] Japan ................... 6-260981

[51] Int. Cl.$^6$ ................... A61B 3/14; A61B 3/10
[52] U.S. Cl. ................... 351/208; 351/211
[58] Field of Search ................... 351/200, 205, 351/206, 208, 201, 245, 211

[56] References Cited

U.S. PATENT DOCUMENTS

| | | | |
|---|---|---|---|
| 4,607,922 | 8/1986 | Humphrey | 351/208 |
| 5,381,194 | 1/1995 | Nishio et al. | 351/208 |
| 5,502,521 | 3/1996 | Katou | 351/208 |

FOREIGN PATENT DOCUMENTS

| | | |
|---|---|---|
| 0 380 260 | 1/1990 | European Pat. Off. . |
| 1-300929 | 12/1989 | Japan . |
| 1-300928 | 12/1989 | Japan . |

*Primary Examiner*—Huy Mai
*Attorney, Agent, or Firm*—Rossi & Associates

[57] ABSTRACT

An ophthalmic apparatus comprising an examining system for examining an eye, wherein the examining system is operated after aligned at a predetermined position with respect to the eye to be examined, comprises the first system for moving the examining system in accordance with operation by an examiner with respect to the eye to be examined, a system for forming alignment indexes on the eye to be examined, a system for detecting the alignment indexes formed on the eye, a system for judging whether or not the alignment indexes detected by the index detecting system are within a predetermined area with respect to the examining system, the second system for further moving the examining system in addition to movement by the first moving system, and a system for controlling, when the judging system judges that the alignment indexes are within a predetermined area, the second moving system to perform alignment based on results from the index detecting system.

14 Claims, 10 Drawing Sheets

OPHTHALMIC APPARATUS PROVIDED WITH ALIGNMENT MECHANISM PRELIMINARY CLASS

BACKGROUND OF THE INVENTION

1. Field of the Invention

The present invention relates to an ophthalmic apparatus and, more particularly to an alignment mechanism provided in the ophthalmic apparatus, which aligns a measuring optical system set in a main unit so as to have a predetermined positional relation with an eye to be examined.

2. Description of Related Art

Ophthalmic apparatuses which perform examination, measurement and the like have an alignment mechanism to align a measuring system and others of the apparatus at a predetermined position with respect to an eye to be examined.

Alignment mechanism of conventional ophthalmic apparatuses is constructed of an alignment index forming optical system for projecting an alignment index onto a cornea of the eye to be examined, an observing optical system for observing the anterior part of the eye and an alignment reticle forming optical system for superimposing an image of reticle on an image of the anterior part under observation through the observing optical system.

For carrying out alignment of the apparatus provided with the alignment mechanism, operators (examiners) have moved the main unit with a joystick and the like with respect to a base table so that the above-mentioned optical systems of the apparatus may be positioned in a predetermined relationship with the eye to be examined. Thus, alignment of the apparatus has been carried out.

The alignment mechanism mentioned above has the advantages of relatively simple construction and easy operation.

However, when using ophthalmic apparatuses needing particularly precise alignment, such as a non-contact type tonometer, operators must perform fine alignment operation. In the case of an inexperienced operator at operating the apparatus, accordingly, there exist problems in that he takes time to operate the apparatus and precise alignment is difficult for him.

SUMMARY OF THE INVENTION

The present invention has been made in view of the above circumstances and has an object to overcome the above problems and to provide an ophthalmic apparatus provided with an alignment mechanism capable of easy and accurate alignment without requiring particular skill of operators.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus provided with an alignment mechanism of this invention comprising an examining means for examining an eye, wherein the examining means is operated after aligned at a predetermined position with respect to the eye to be examined, the apparatus comprising the first means for moving the examining means in accordance with operation by an examiner with respect to the eye to be examined, means for forming alignment indexes on the eye to be examined, means for detecting the alignment indexes formed on the eye, means for judging whether or not the alignment indexes detected by the index detecting means are within a predetermined area with respect to the examining means, the second means for further moving the examining means in addition to movement by the first moving means, and means fop controlling, when the judging means judges that the alignment indexes are within a predetermined area, the second moving means to perform alignment based on results from the index detecting means.

According to the present invention, an examiner does not have to take care the position of the measuring part at every alignment, lightening the burden imposed on the examiner.

The measuring part is located at a reference position at the start of alignment, so that it may not contact the eye or nose of the examinee during operation of the first moving means, thus improving safety. The apparatus according to the present invention also enables rapid measurement regardless of levels of examiner's skill in alignment operation.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

FIG. 5($b$) is a plane view of a mask of the movement mechanism shown in FIG. 4;

DETAILED DESCRIPTION OF THE PREFERRED EMBODIMENTS

A detailed description of one preferred embodiment of an ophthalmic apparatus provided with an alignment mechanism embodying the present invention will now be given referring to the accompanying drawings.

Figure 1:
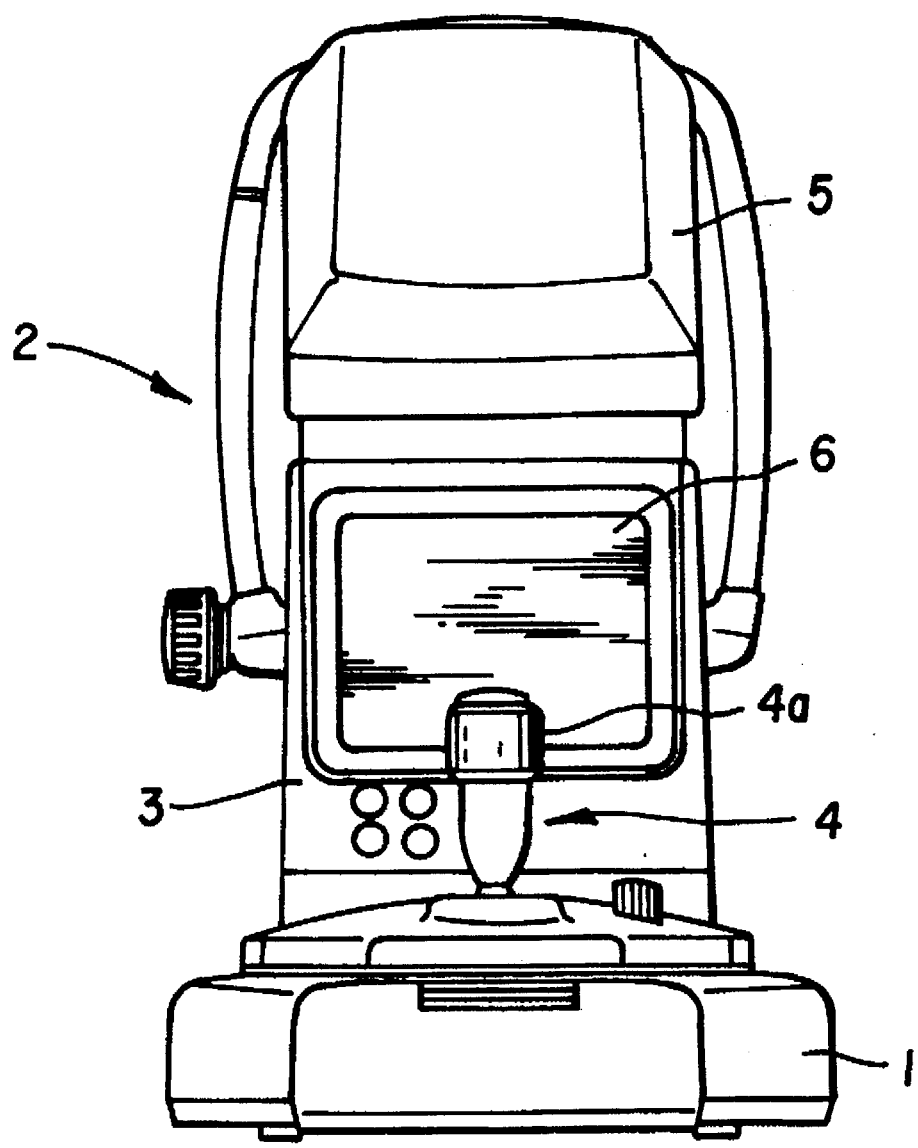
FIG. 1 is a front view of an apparatus in an embodiment according to the present invention, which is a side to be viewed by an operator.
Figure 2:
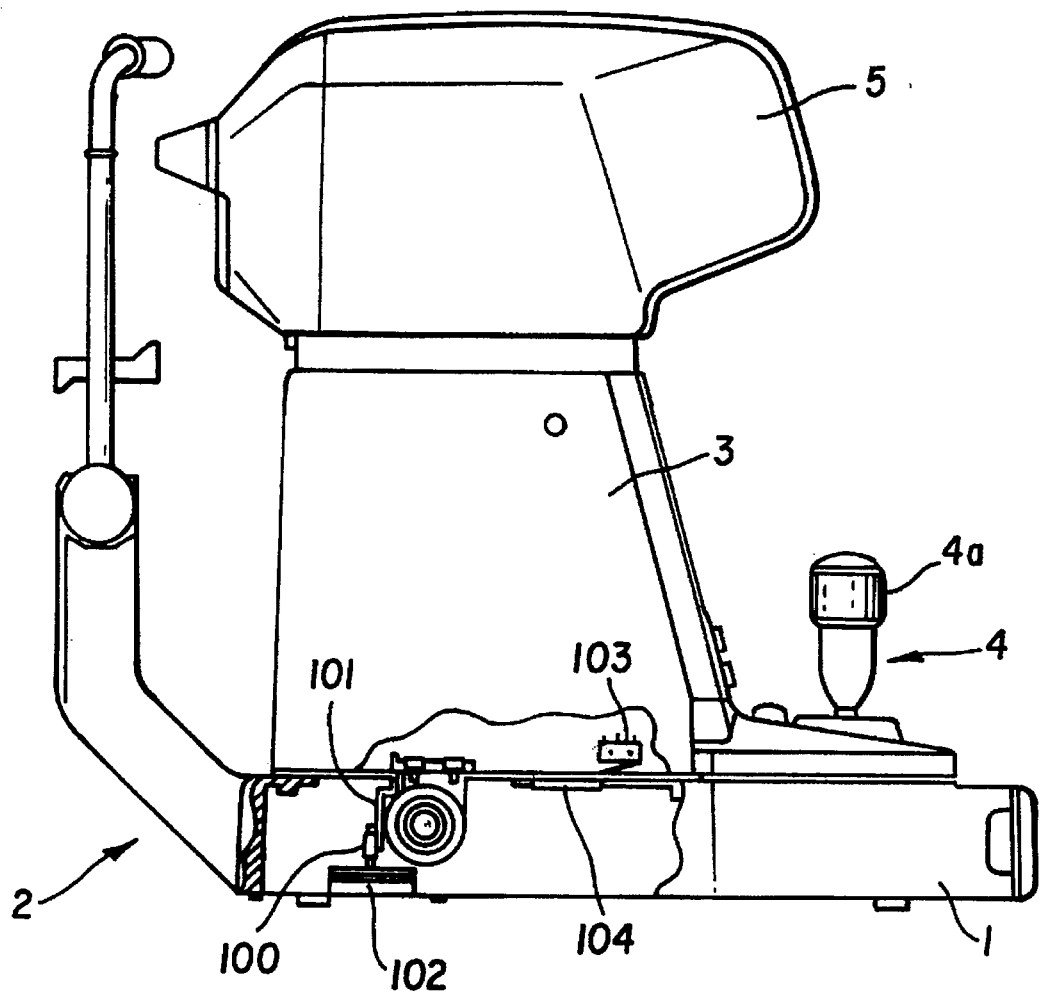
FIG. 2 is a left side view of the apparatus of FIG. 1, which is partially cutaway.

FIG. 1 is a front view of a non-contact type tonometer in an embodiment of the present invention, which shows a side viewed by an examiner (operator). FIG. 2 is a left side view of the tonometer, which is partially cutaway.

The non-contact type tonometer is externally provided with mainly a base 1, a head support 2 for fixedly supporting the eye to be examined, connected to the base 1, a main body 3 movable in each of a lateral and a longitudinal directions on a horizontal plane of the base 1, which is to be moved in accordance with operation of a joystick 4 having a mechanism mentioned later, a measuring part 5 in which a measuring system and an optical system mentioned later are provided and a TV monitor 6 for displaying an anterior part of the eye to be examined to allow the examiner to observe it and information including alignment information, measuring data and others, to be given to the examiner.

The measuring part 5 is movable in a vertical direction with respect to the main body 3 in accordance with operation of a rotating knob 4a of the joystick 4 by the examiner. In automatic alignment the measuring part 5 is further movable from a reference position in a lateral and a longitudinal directions (hereinafter called an original position) by 5 mm in the right and the left directions respectively (28 mm (±14 mm) in a vertical direction) and about 5 mm in a front direction, i.e., toward the eye to be examined.

The apparatus of the present embodiment is mainly constructed of an alignment optical system, a joystick mechanism, a position detecting mechanism for detecting positions of right and left eyes and a backward position in order to return the measuring part 5 to the original position and a control system. They will be separately described hereinafter.

Non-contact type tonometers are used for measurement of the tension of the eye, in which compressed air is jetted to a cornea of the eye to be examined to thereby deform the cornea, the deformation of the cornea into a predetermined state is detected and the air pressure when the cornea is deformed into a predetermined state is directly or indirectly detected, and the tension of the eye is measured based on the air pressure consequently. The measuring mechanism itself of the apparatus is, however, less related to the present invention and therefore the description in U.S. Pat. No. 5,279,300 proposed by the same inventors as the present invention, the title of which is "NONCONTACT TYPE TONOMETER", is utilized in this specification.

Alignment Optical System

Figure 3:
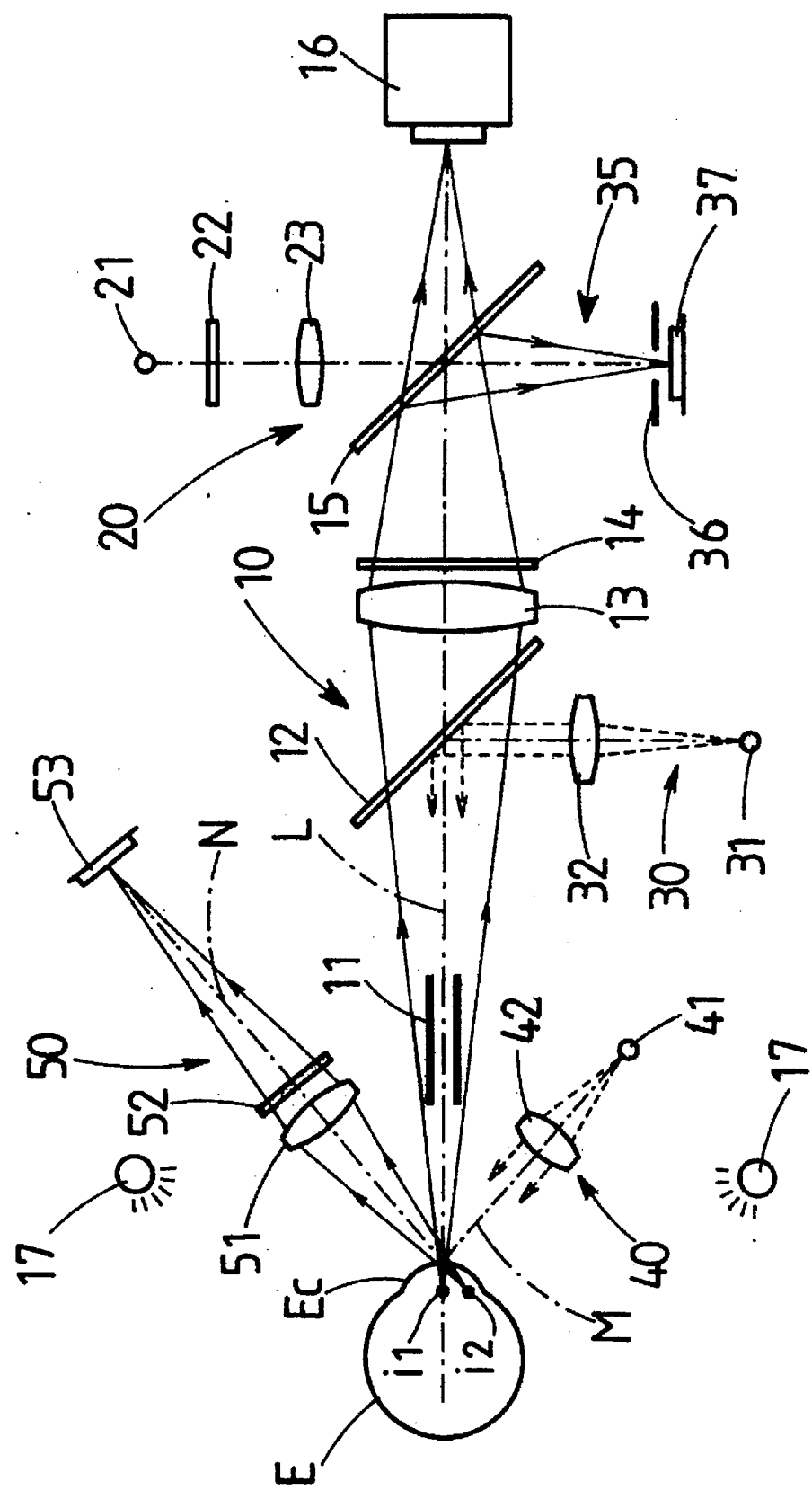
FIG. 3 is a schematic top view of an alignment optical system of the apparatus of FIG. 1.

FIG. 3 is a top view of an alignment optical system of the apparatus in the embodiment. The alignment optical system will be described separately into an observing optical system, a reticle projecting optical system, a front index projecting optical system, a front index detecting optical system, a distance index projecting optical system and a distance index detecting optical system.

Observing Optical System

The observing optical system 10 has an optical axis L and is provided on the optical path thereof with a nozzle 11 for jetting air to deform a cornea, an axis of the nozzle 11 being coincide with the axis L. The observing optical system 10 is further provided, on the optical axis L, with a half mirror 12, an objective lens 13, a filter 14, a half mirror 15 and a TV camera 16. The filter 14 has characteristics of transmitting a wavelength of luminous flux of the front index projecting optical system 30 and not transmitting a wavelength of luminous flux of the distance index projecting optical system 40, thereby preventing an unnecessary noise light from reaching to the TV camera 16 and a detecting element of the front index detecting optical system 35.

Numeral 17 is an illumination light source which emits a near-infrared light for observation of the eye to be examined. The light emitted from the illumination light source 17 illuminates the eye E to be examined, forming an image of the anterior part of the eye E on a surface of an imaging element of the TV camera 16 by the objective lens 13 via the half mirror 12, the filter 14 and the half mirror 15.

Reticle Projecting Optical System

The reticle projecting optical system 20 is constituted of a light source 21, a reticle plate 22 provided with a ring mark and a projecting lens 23. A reticle of the reticle plate 22 illuminated by the light source 21 forms an image on the imaging surface of the TV camera 16 by the projecting lens 23 via the half mirror 15. The image of the reticle is then displayed on the TV monitor 6 as superimposed on the image of the anterior part of the eye.

Front Index Projecting Optical System

The front index projecting optical system 30 is constituted of a light source 31 such as a near-infrared LED which emits a light of a wavelength near to that of the illumination light source 17, and a projecting lens 32.

The light source 31 is applied with modulation on its output by a predetermined frequency in order to prevent the luminous flux of the illumination light source 17 from becoming noise to the front index detecting optical system.

Light emitted from the light source 31 becomes into parallel luminous flux by the projecting lens 32, reflected by the half mirror 12, and transmitted through the inside of the nozzle 11 or others along the optical axis L to irradiate the cornea Ec. The luminous flux is directed by mirror reflection on the cornea Ec to form an index i1 which is a virtual image of the light source 31 in the eye E. Luminous flux of the index i1 forms an image of the index i1 on the imaging element of the TV camera 16 through the observing optical system.

Front Index Detecting Optical System

The front index detecting optical system 35 is provided with a field stop 36, a two-dimensional position detecting element 37 and components used partially in common with the observing optical system 10, namely, the objective lens 13, the filter 14 and the half mirror 15. The field stop 36 has a diameter designed so as not to allow an unnecessary light to be incident into the detecting element 37 and so as to allow luminous flux of the index i1 being at an approximately proper position with respect to the reticle image formed on the imaging element of the TV camera 16 to be incident into the detecting element 37. As the two-dimensional position detecting element 37, various sensors such as a CCD, a PSD (Position Sensor Detector), etc. may be used. The two-dimensional position detecting element may be substituted with an optical detecting element of a two-divided or four-divided type.

Luminous flux of the front index is specularly reflected by the cornea Ec, guided by the half mirror 15 to the front index detecting optical system 35, passed through the field stop 36 and received at the detecting element 37. The detecting element 37 will then detect the position of the eye to be examined in a lateral and a vertical directions with respect to the measuring axis (the observing optical axis L) based on a two-dimensional position of the luminous flux of the index i1 incident onto the sensing surface of the detecting element Distance Index Projecting Optical System The distance index projecting optical system 40 is constituted of a light source 41 such as a LED having a wavelength different from the light source 31 of the front index projecting optical system 30 and a projecting lens 42, both components being arranged on an optical axis denoted by character M in FIG. 3. This optical axis M is designed so as to incline related to the optical axis L and both axes M and L intersect with each other at a point apart from the nozzle 11 by a predetermined working distance. It is preferable to determine an intersecting angle of the optical axis M with respect to the optical axis L in the range of 20° to 40°.

Light emitted from the light source 41 becomes into parallel rays through the projecting lens 42 and is directed along the optical axis M to irradiate the cornea Ec. The luminous flux specularly reflected by the cornea Ec forms an index i2 which is a virtual image of the light source 41.

Distance Index Detecting Optical System

The distance index detecting optical system 50 comprises a light receiving lens 51, a filter 52 and a one-dimensional position detecting element 53, which are arranged on an optical axis denoted by character N. The optical axis N is at a symmetrical position with the optical axis M about the optical axis L, and the optical axis N intersects the optical axis M on the optical axis L. The filter 52 has optical characteristics of allowing a light of a wavelength of the light source 41 of the distance index projecting optical system 40 to pass therethrough, but not allowing lights of wavelengths of the illumination light source 17 and the light source 31 of the front index projecting optical system 30 to pass, thereby preventing lights of the index i1 and the illumination light source 17 which become possibly noise from being incident on the one-dimensional position detecting element 53.

The corneal reflection light from the light source 41 forming the index i2 is directed by the light receiving lens 51 through the filter 52 to the one-dimensional position detecting element 53. When the eye E moves in a direction along the optical axis L (a longitudinal direction), the image of the index i2 being formed by the light receiving lens 51 moves in a detecting direction of the one-dimensional position detecting element 53 at the same time. Based on the displacement quantity of the index image on the one-dimensional position detecting element 53, the position of the eye E to be examined in a longitudinal direction is detected.

A cylindrical lens having a generatrix in the detecting direction of the one-dimensional position detecting element 53 may be disposed forwardly of the detecting element 53.

Joystick Mechanism

A joystick mechanism has a moving mechanism for moving the main body 3 with a joystick 4 in each of a lateral, a longitudinal and a vertical directions and a brake mechanism for controlling the movement of the main body 3 with the joystick 4.

Figure 4:
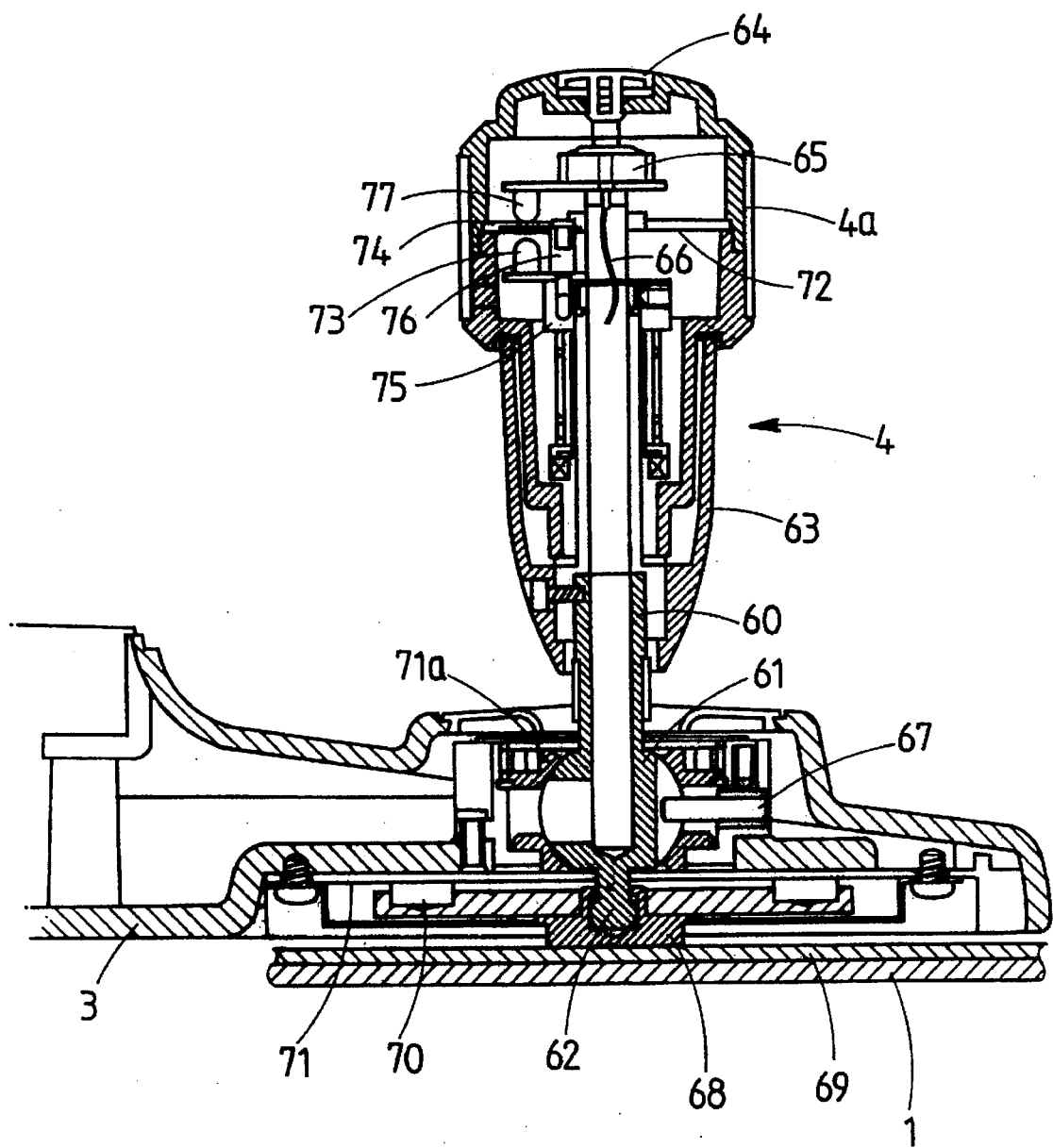
FIG. 4 is a cross sectional view of a joystick of the apparatus of FIG. 1, showing a movement mechanism of the apparatus.

FIG. 4 is a sectional view of the joystick 4 to explain the moving mechanism.

The joystick 4 is provided with a shaft 60 inserted therein, the shaft 60 being formed of at the lower part a spherical part 61 and a spherical lower part 62. The joystick 4 further comprises a swing knob 63 for swing the joystick 4, which is secured to the shaft 60. The rotating knob 4a of the joystick 4 is provided at its top portion with a button 64 to thereby generate a trigger signal by manual operation. The swing knob 63 is provided with a switch 65. When the button 64 is pressed, the switch 65 works to transmit a signal through an electric wire 66 to a control circuit mentioned later, and thus measurement starts.

The main body 3 is movable through a sliding plate 68 in a horizontal direction on a friction plate 69 put on the base 1. Numeral 70 denotes a slip plate secured on the sliding plate 68 and numeral 71 designates a plate fixed to the main body 3 with screws or the like. When the swing knob 63 is swung, the shaft 60 is swung about the center of the spherical part 61 as fulcrum through a spherical bearing 71a and, accordingly, the lower part 62 of the shaft 60 causes the sliding plate 68 to vibrate. The material of each plate is selected so that the frictional force between the sliding plate 68 and the friction plate 69 becomes larger than the frictional force between the plate 71 and the slip plate 70.

Moving the measuring part 5 in a vertical direction with the rotating knob 4a will be conducted as follows.

Figure 5:
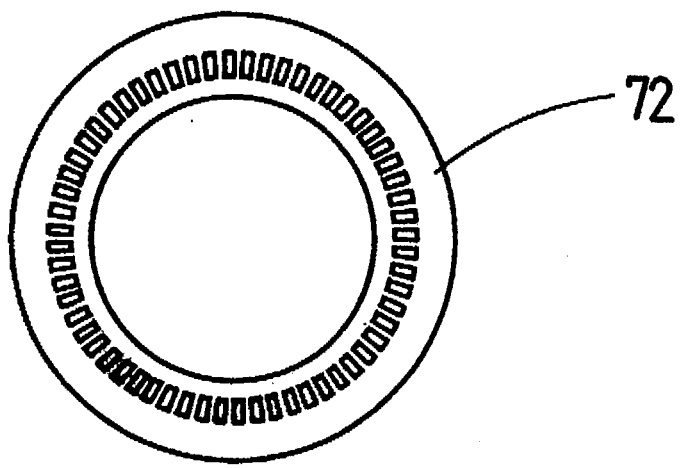
FIG. 5($a$) is a plane view of a disc of the movement mechanism shown in FIG. 4.
Figure 5:
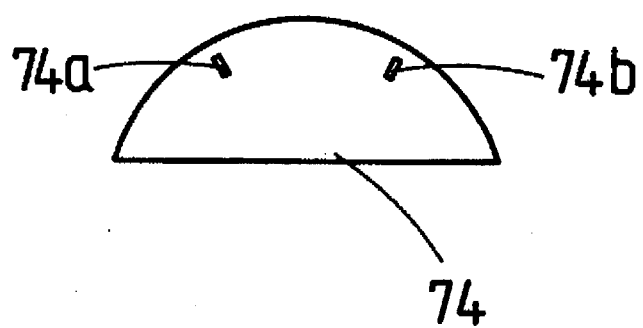

The rotating knob 4a is provided with a disk 72 having a plurality of slits as shown in FIG. 5(a), which is secured inside the rotating knob 4a and therefore rotatable at the same time when the rotating knob 4a is rotated. Numeral 73 denotes a LED mounted on the shaft 60 and numeral 74 designates a mask having two slits as shown in FIG. 5(b), secured to the shaft 60 with a nut 75 and a pin 76. Numeral 77 denotes a photo-transistor mounted on the shaft 60 with the nut 75. Two LEDs 73 (a, b) and two photo-transistors 77 (a, b) are disposed in two sets of each one so as to put the mask 74 between the LED 73 and the photo-transistor 77. Each set is arranged at each position corresponding to slits 74a and 74b respectively. The slits 74a and 74b of the mask 74 are further arranged at positions where output waveforms of the photo-transistors 77a and 77b are displaced by a half-cycle. The output waveforms of the photo-transistors 77a and 77b are shown in FIG. 6. Lights of the LEDs 73a and 73b passed through the slits 74a and 74b of the mask 74 are intermittently irradiated to the photo-transistors 77a and 77b according to the rotation of the disk 72. Rotating direction and rotating quantity of the rotating knob 4a are detected based on the output waveforms of the photo-transistors 77a and 77b at a detecting circuit not shown in the figure.

Figure 6A:
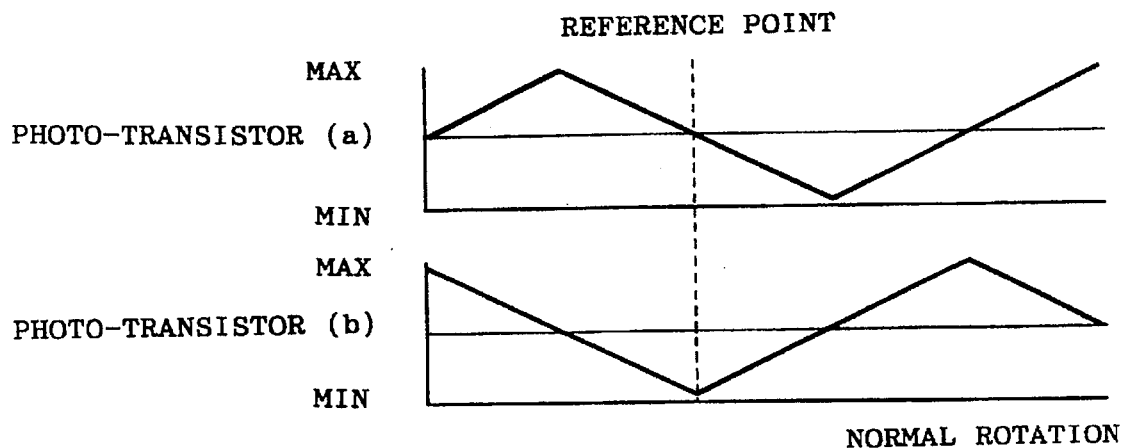
FIG. 6($a$) and ($b$) are graphical diagrams of output waveforms of photo-transistors set in the joystick, (a) showing output waveforms at the time of the normal rotation of a rotating knob and (b) showing output waveforms at the time of the reverse rotation of same.
Figure 6B:
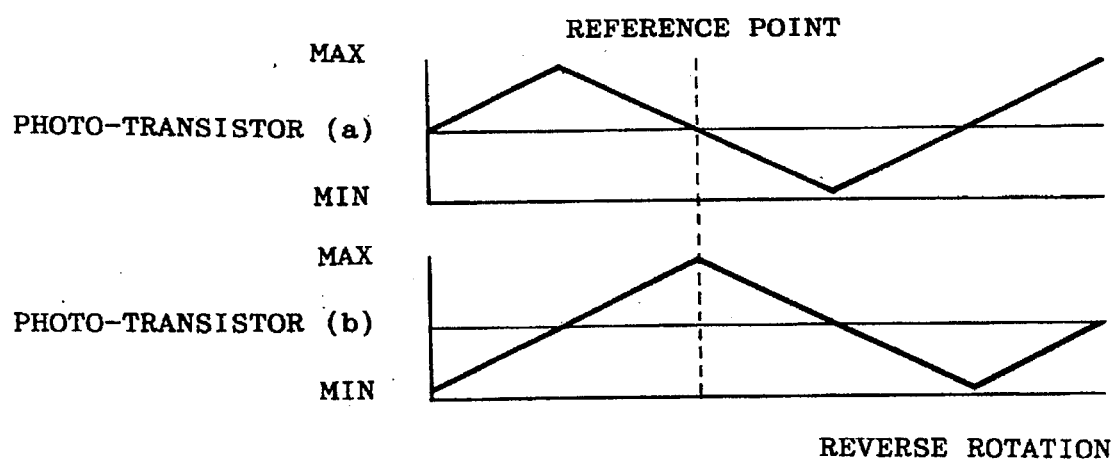

Rotating direction of the rotating knob 4a can be detected by detecting an output condition of the photo-transistor 77b (or 77a) at a reference point compared with a waveform of the photo-transistors 77a (or 77b) at a predetermined reference point. In the case of taking a reference point as shown in FIG. 6, it is judged that when the output of the photo-transistors 77b at the reference point is minimum as shown in FIG. 6(a), it indicates the normal rotation of the rotating knob 4a and, alternatively, when the output is maximum as shown in FIG. 6(b), it indicates the reverse rotation.

Rotating quantity of the rotating knob 4a is detected by counting the number of cyclic waveforms from a reference point to the next reference point within a predetermined time based on the output of the photo-transistors 77a (or 77b).

With voltage corresponding to the rotating direction and the rotating quantity detected by a detecting circuit not illustrated, the control circuit drives a driving system mentioned later to move the measuring part 5 in a vertical direction.

Next, a brake mechanism will be described referring to FIG. 7. The main body 3 is provided, fixedly at its lower end, with a movable base 80 through a base portion 80a. The movable base 80 supports rotatably a guide pipe 82 through a bearing 81. The guide pipe 82 is also supported through a bearing 83 so as to be slidable in the axis direction of a horizontal shaft 84. At both ends of the horizontal shaft 84, wheels 85 are secured respectively. These wheels 85 roll forward or backward on a guide plate 86 disposed on a bottom portion of the base 1. The main body 3 can accordingly move in each of a lateral and a longitudinal directions in accordance with operation of the joystick 4 as mentioned above. As shown in the enlarged figure of FIG. 7, numeral 90 denotes a piezoactuator mounted on the guide pipe 82, numeral 91 designates a brake plate having a supporting point 91a fixed to the guide pipe 82. When applied with voltage, the piezoactuator 90 extends to press an upper end of the brake plate 91. The brake plate 91 turns about the supporting point 91a and presses the horizontal shaft 84 by the lower end of the brake plate 91 owing to leverage. This pressing puts a brake on the movement of the guide pipe 82, thereby restraining the movement of the main body 3 in a lateral direction, i.e., a right and left direction. Numeral 92 designates a solenoid embedded in one end of the horizontal shaft 84 and numeral 93 is a pin of the solenoid 92. Numeral 94 denotes a friction plate secured in the base 1. When the pin 93 is pushed out by activation of the solenoid 92, the pin 93 comes into contact with the friction plate 94 to restrain the rolling of the horizontal shaft 84. Consequently, the movement of the main body 3 in a longitudinal direction, i.e., a front and back direction is restrained. This brake mechanism is driven by a control circuit mentioned later in automatic alignment.

Both Eyes and Back Position Detecting System

Figure 7:
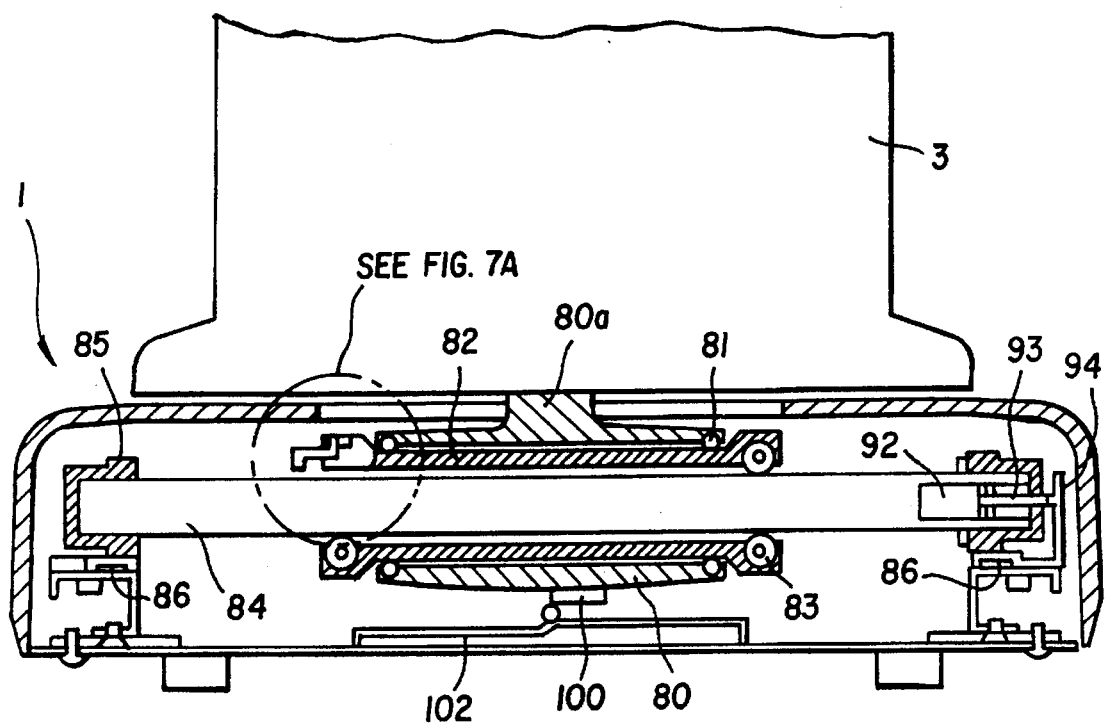
FIG. 7 is a partially sectional view with a partially enlarged view showing a brake mechanism of the apparatus.
Figure 7A:
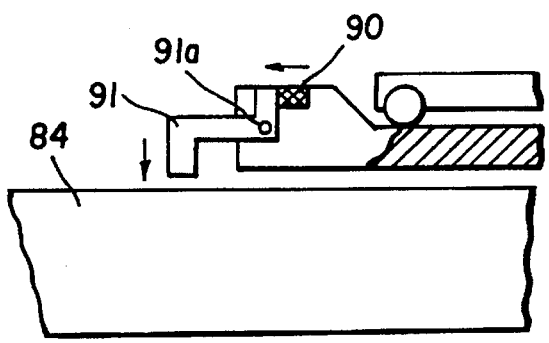

Numeral 100 in FIG. 2 and FIG. 7 is a microswitch for detecting a right and a left eyes. The microswitch 100 is connected with the main body 3 with a mounting plate 101. Numeral 102 denotes a guide plate installed in a lower part within the base 1, which is formed so that the right side thereof (in FIG. 7) is higher from the center in a lateral direction of the base 1 than another side. In the course of the movement of the main body 3 in a lateral direction, the microswitch 100 is applied with electricity when it is on the right side of the guide plate 102. The center of right and left eyes of an examinee supported on the head support 2 is in keeping with the center of the base 1, so that a right or left eye of the examinee is detected based on a signal generated from the microswitch 100. The signal of the detecting mechanism for detecting a right or a left eye of an examinee serves as a signal to move the driving mechanism for moving the measuring part 5 in each of a lateral, a longitudinal and a vertical directions, at an original position, as well as to judge whether an eye to be examined is right or left.

Numeral 103 in FIG. 2 is a microswitch for detecting a back end, namely, the nearest position to the examiner. This microswitch 103 is mounted in the main body 3. Numeral 104 is a microswitch guide plate fixed in the base 1, which is located so that a contact of the microswitch 103 is pushed up when the main body 3 comes at the most back end of a movable area in a front and back direction, thereby electricity being applied to. The signal of the microswitch 103 is used as a signal to move the measuring part 5 at each original position in each of a lateral, a longitudinal and a vertical directions.

In the present embodiment, in addition to the signal of the microswitch 103, a signal of a print switch and an electric power charging signal are used as a signal to move the measuring part 5 at the original position.

Control System

Figure 8:
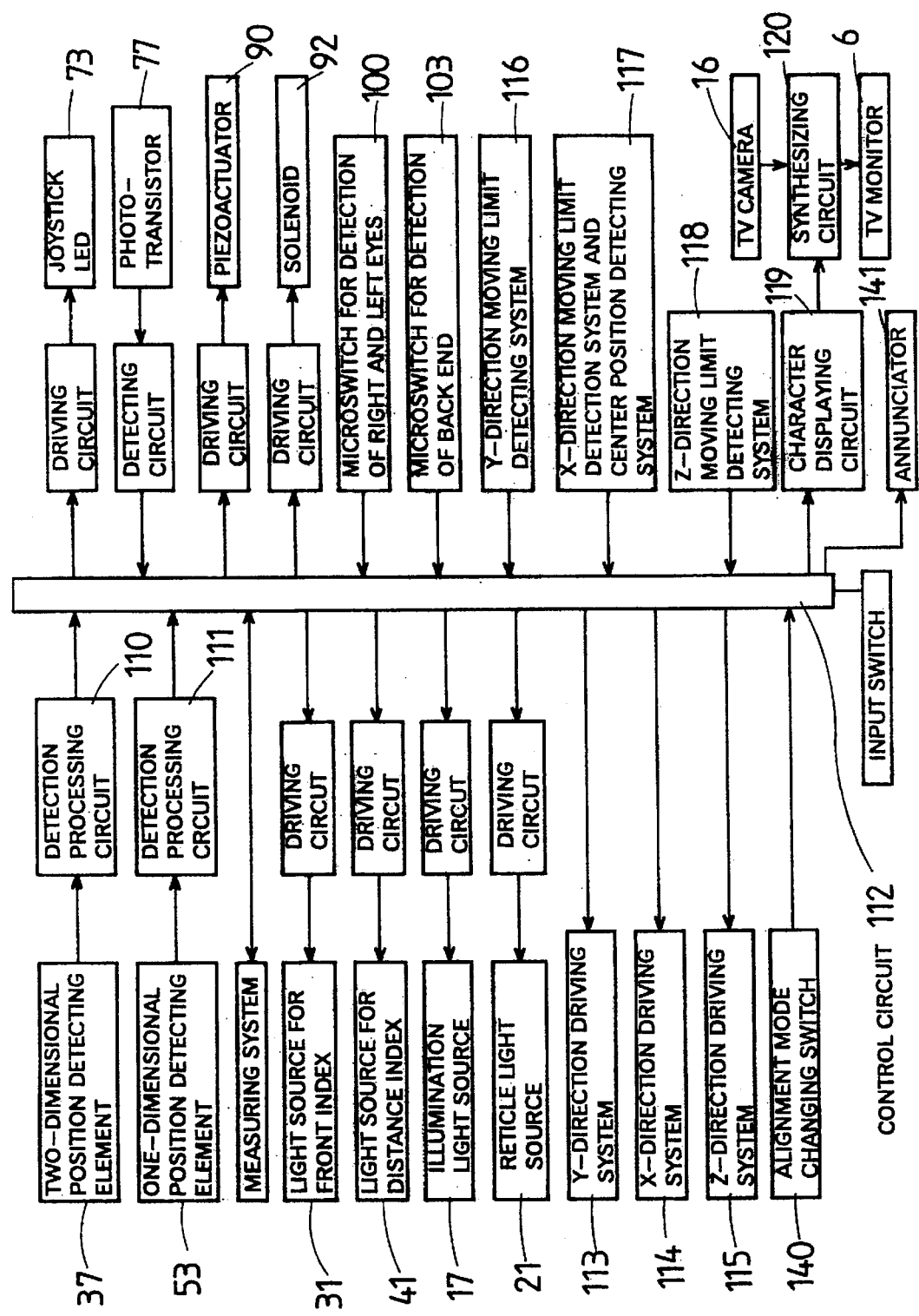
FIG. 8 is a block diagram showing a main part of a control system of the apparatus according to the present invention.

FIG. 8 is a block diagram showing a main part of the control system in the present embodiment.

Signals from the two-dimensional position detecting element 37 of the front index detecting optical system and the one-dimensional position detecting element 53 of the distance index detecting optical system are processed at detection processing circuits 110 and 111 respectively, and then input to a control circuit 112. The control circuit 112 applies the signals with a known process to obtain the displacement quantity of the eye E to be examined in each of a lateral, a longitudinal and a vertical directions from a proper position of the eye E.

Numeral 113 denotes a Y-direction driving system fop moving the measuring part 5 in a vertical direction (Y-direction), numeral 114 designates a X-direction driving system for moving same in a lateral (right and left) direction (X-direction) and numeral 115 denotes a Z-direction driving system for moving same in a longitudinal (front and back) direction (Z-direction). Each of the driving systems is constructed of a motor and a motor driving circuit and is driven based on the signals of displacement information in each direction input to the control circuit 112.

When the control circuit 112 is input with a signal from the microswitch 100 for detecting a right or a left eye to be examined or a signal from the microswitch 103 for detecting the back end, it drives each of driving systems 113, 114 and 115 to move the measuring part 5 at the original position.

The original positions of the measuring part 5 in X- and Y-directions is located at substantially a center in a movable area of the measuring part 5. The original position of same in a Z-direction are located at the nearest point to an examiner. A movable area in the Y-direction is relatively wide and there is no danger that the movement of the measuring part 5 in the Y-direction causes harm to the examinee, therefore the measuring part 5 may be returned at the original positions in the X-, Y- and Z-directions at only the time of charging electric power or printing out and at the original positions in the X- and Z-directions at the time of changing a right and left eyes to be examined.

Numeral 116 denotes a system for detecting a moving limit of the measuring part 5 in a Y-direction, 117 designates a system for detecting a moving limit of the measuring part 5 in a X-direction and a center position in a lateral direction and 118 denotes a system for detecting a moving limit of same in a Z-direction. Each of detecting systems is constructed of a sensor of transparent type and a shading plate or a microswitch and the like. Numeral 119 designates a character displaying circuit for generating graphics, letters and the like for alignment and 120 denotes a synthesizing circuit for synthesizing a picture signal of the TV camera 16 and a signal of the character displaying circuit 119.

The control circuit 112 transmits the signal of displacement information in a longitudinal direction to the character displaying circuit 119. Based on this signal, the circuit 119 generates a graphic signal of a distance mark and a positional signal on the TV monitor 6. Signals generated by the character displaying circuit 119 are synthesized with a picture signal of the TV camera 16 at the synthesizing circuit 120 and are output on the TV monitor 6. The distance mark moves in real-time above or below a reticle image 131 displayed on the TV monitor 6 according to a distance between the nozzle 11 and the cornea Ec.

Figure 9:
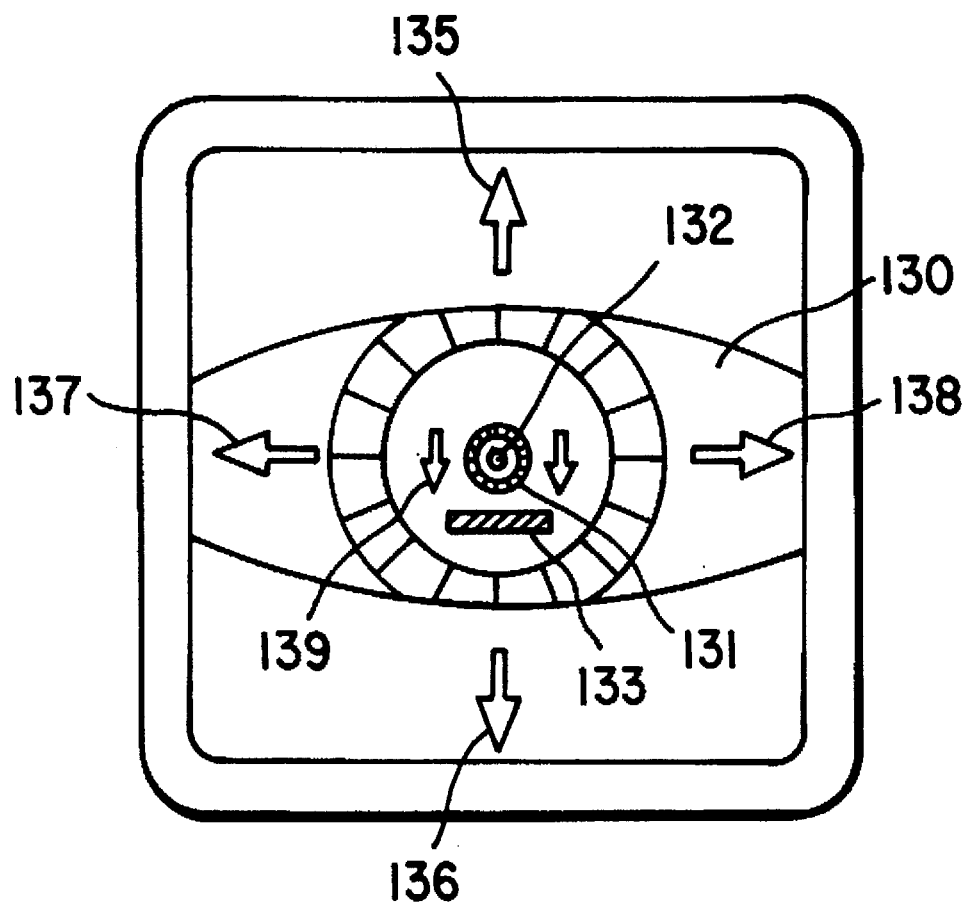
FIG. 9 is a view to explain a picture displayed on a TV monitor 6 of the alignment optical system shown in FIG. 3.

FIG. 9 shows a displayed picture on the TV monitor 6. In the figure, numeral 130 denotes an image of the anterior part of the eye to be examined, numeral 131 designates an image of a reticle, numeral 132 denotes an image of the front index and numeral 133 designates a distance mark. Numerals 135–139 designate indicating marks to inform evading operation to the examiner when movement of each driving system under automatic alignment comes to each limit, those marks being generated based on signals from the character displaying circuit 119. The indicating marks 135–139 show, respectively, a direction in which the measuring part 5 must be moved by manual operation; the mark 135 indicates an upward direction, the mark 136 shows a downward direction, the mark 137 indicates a left direction, the mark 138 shows a right direction and the marks 139 indicate a back direction (or a front direction if the marks are displayed reversely).

Figure 10:
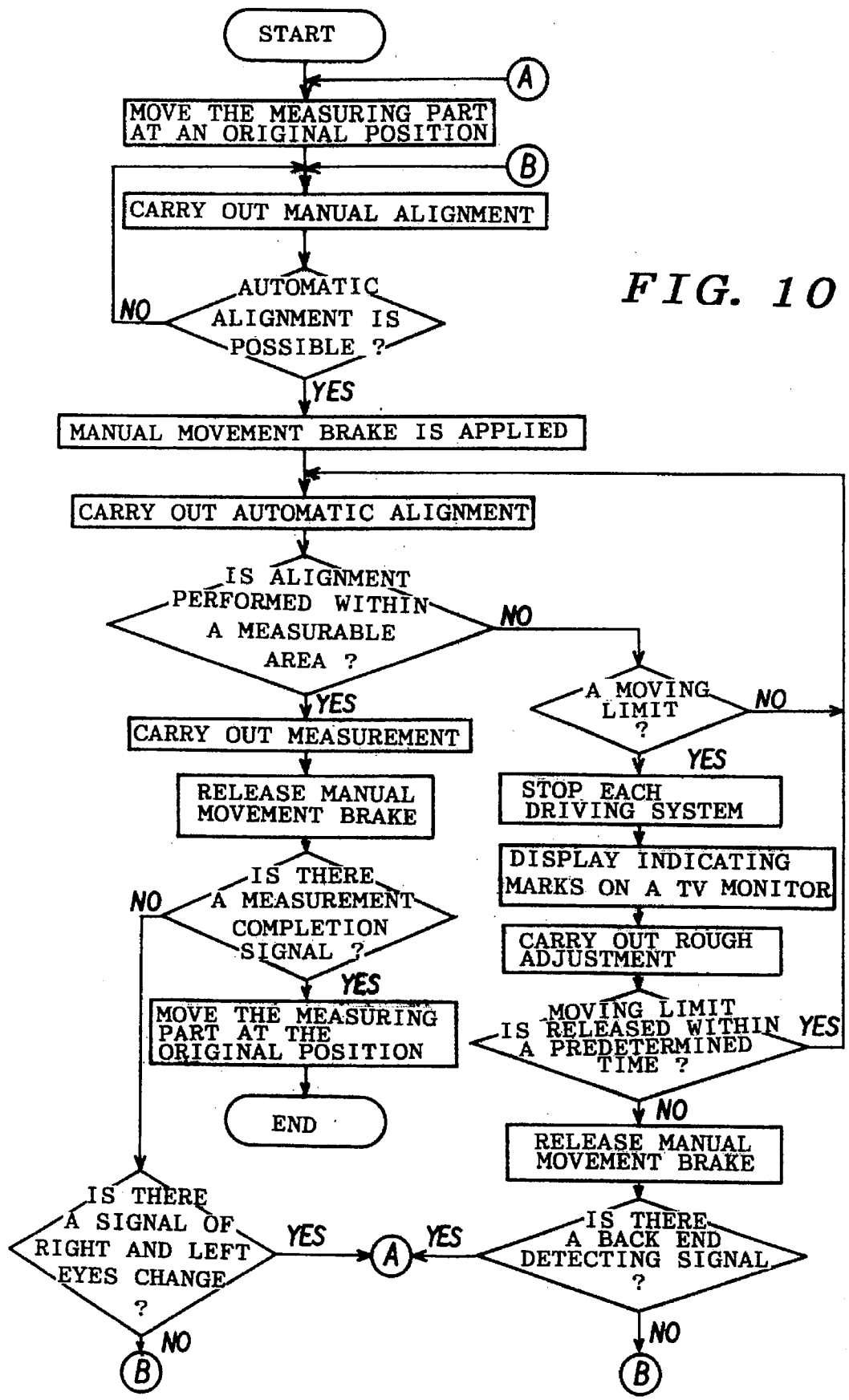
FIG. 10 is a flow chart explaining operation of the apparatus.

Operation of the apparatus constructed as above will be described below referring to FIG. 10 which is a flow chart thereof.

In the apparatus, either alignment modes, manual or automatic, may be selected by an alignment mode changing switch 140. In this embodiment the automatic alignment mode is selected.

When electric power is charged to, the control circuit 112 drives the X-, Y- and Z-driving systems 113–115, respectively, to return the measuring part 5 at the original position in relation to the main body 3. In movement to the original position, the measuring part 5 is moved in each direction until it is detected by each of moving limit detecting systems 116–118 sequentially, thereafter each of X- and Y-direction driving systems is returned by the predetermined number of pulses. The position of the measuring part 5 can be detected if the number of pulses of the movement is memorized, and its positional information may be used in subsequent movements to the original position.

The examinee puts his head on the head support 2 to fix his eyes at a predetermined position. The examiner carries out rough alignment by operating the joystick 4. This rough alignment is performed in a manner described as follows.

An image of the anterior part of the eye E to be examined illuminated by a light from the illumination light source 17 is received at the TV camera 16, as well as a reticle image provided by the reticle optical system, and displayed on the TV monitor 6. While observing the anterior part image 130 and the reticle image 131 displayed on the TV monitor 6, the examiner operates the joystick 4 and the rotating knob 4a to move the main body 3 in a lateral and longitudinal direction with respect to the base 1 and to move the measuring part 5 in a vertical direction with respect to the main body 3, so as to adjust the circular reticle image 131 near a center of iris or pupil of the anterior part image of the eye.

In such a way, when an index image i1 is formed on the TV monitor 6, the two-dimensional detecting element 37 can detect the index image i1, becoming in a condition that automatic alignment can be performed in a vertical and a lateral directions.

When luminous flux of the index image i2 is incident onto the one-dimensional detecting element 53, it comes to a condition that automatic alignment in a longitudinal direction can be performed, at that time, a distance mark 133 is displayed on the TV monitor 6.

When the automatic alignment in each of a vertical, a lateral and a longitudinal directions is in a condition to start, the control circuit 112 activates the piezoactuator 90 and the solenoid 92 to restrain movement of the main body 3 in a lateral and a longitudinal directions respectively. The piezoactuator 90 and the solenoid 92 may be activated individually in each direction where automatic alignment can be done. After rough alignment is completed in the above manner, automatic alignment is carried out.

In automatic alignment, the control circuit 112 obtains each amount of deviation of the apparatus in a lateral, a longitudinal and a vertical directions with respect to the position of when the eye E is in a proper position, based on output signals from the two-dimensional detecting element 37 and the one-dimensional detecting element 53 respectively. Based on the deviation information, the control circuit 112 drives the X-direction driving system 114, the Y-direction driving system 113 and the Z-direction driving system 115, respectively.

As the measuring part 5 is moved by each driving system with respect to the main body 3, each index image moves on the two-dimensional detecting element 37 or the one-dimensional detecting element 53. The control circuit 112 judges whether or not each index image enters within each predetermined permissible area. When judged each index image is within the permissible area, the control circuit 112 stops to drive each driving system, so that alignment is completed. Subsequently, the control circuit 112 generates a signal to start measurement to thereby drive the measuring system.

When each of moving limit detecting systems 116 to 118 detects that the measuring part 5 reached each moving limit while the index images do not enter within the permissible area of alignment completion, the driving system for automatic alignment is stopped. The control circuit 112 displays the indicating mark(s) 135–139 on the TV monitor 6 and at the same time drives an annunciator 141 to inform the examiner of the direction(s) in which the measuring part 5 must be moved. On releasing the moving limit by rough adjustment of alignment by the examiner, automatic alignment is operated again. In a case that the moving limit can not be released within a predetermined time by the rough adjustment of alignment, brakes by the piezoactuator 90 and the solenoid 92 are released. The brakes may be released by switch operation by the examiner.

To return the main body 3 and the measuring part 5 to an initial state, the examiner returns the joystick 4 to the examiner's side. When detecting by operation of the microswitch 103 that the main body 3 reaches the most back end in a longitudinal direction, the control circuit 112 drives the X-, Y- and Z-direction driving systems 113–115 respectively (or each driving system except for Y-driving system) to position the measuring part 5 at the original position with respect to the main body 3. Positioning the measuring part 5 as described above enables of avoiding the danger of contact of the nozzle to the eye to be examined and retaining movable directions of the measuring part 5. The examiner then starts alignment again.

At the time when brakes are removed but the examiner does not return the joystick 4 to the examiner's side, the examiner operates the joystick 4 to move the measuring part 5 at a position where the two-dimensional detecting element 37 and the one-dimensional detecting element 53 detect index images respectively, to thereby start automatic alignment.

When the alignment and one-time measurement operation are completed, brakes by the piezoactuator 90 and the solenoid 92 are released. The control circuit 112 detects whether or not a measurement completion signal is generated with a print switch and the like. When received the measurement completion signal, the control circuit 112 moves the measuring part 5 at the original position through each of X-, Y- and Z-direction driving systems 113–115. If not received, alternatively, a measurement completion signal, the control circuit 112 detects whether or not a signal to change right and left eyes to be examined is input into with the microswitch 100. When detects a signal to change right and left eyes to be examined, the control circuit 112 drives X-, Y- and Z-direction driving systems 113–115 to move the measuring part 5 at the original position. If the right and left eyes changing signal is not detected, alternatively, alignment is repeated to perform measurement again.

The present invention may be embodied in other specific forms without departing from the spirit or essential characteristics thereof, for instance, according to degree of a permissible area of alignment and kind of measuring methods.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising an examining means for examining an eye, wherein said examining means is operated after aligned at a predetermined position with respect to the eye to be examined, the apparatus comprising:

first means for moving said examining means in accordance with operation by an examiner with respect to the eye to be examined;

means for irradiating alignment lights onto a cornea of the eye to be examined to form alignment indexes formed by the reflection of the alignment lights from the surface of the cornea;

means for detecting a position of the alignment indexes formed on the eye;

second means for further moving said examining means;

means for judging whether or not said examining means is within a predetermined rough alignment area in X, Y and Z directions, where said second moving means starts to move, with respect to the eye based on results from said index detecting means; and means for controlling said second moving means to perform alignment, when said judging means judges that said examining means is within the predetermined rough alignment area in X, Y and Z directions.

2. An ophthalmic apparatus provided with an alignment mechanism according to claim 1, further comprising means for observing an image of an anterior part of the eye to be examined and means for forming indexes so as to superimpose on the image of the anterior part of the eye under observation through said observing means, thereby to inform a direction in which the examining means must be moved by said first moving means.

3. An ophthalmic apparatus provided with an alignment mechanism according to claim 1, further comprising means for returning said examining means to a basic position of said second moving means.

4. An ophthalmic apparatus provided with an alignment mechanism according to claim 1, wherein the apparatus comprises a non-contact tonometer.

5. An ophthalmic apparatus comprising an examining means for examining an eye, wherein said examining means is operated after aligned at a predetermined position with respect to the eye to be examined, the apparatus comprising:

first means for moving said examining means in accordance with operation by an examiner with respect to the eye to be examined;

means for irradiating alignment lights onto a cornea of the eye to be examined to form alignment indexes formed by the reflection of the alignment lights from the surface of the cornea;

means for detecting a position of the alignment indexes formed on the eye;

second means for further moving said examining means;

means for judging whether or not said examining means is within a predetermined rough alignment area in X, Y and Z directions, where said second moving means starts to move, with respect to the eye based on results from said index detecting means;

means for controlling said second moving means to perform alignment, when said judging means judges that said examining means is within the predetermined rough alignment area in X, Y and Z directions; and means for restraining movement of the first moving means when said judging means judges the indexes are within the predetermined rough alignment area.

6. An ophthalmic apparatus provided with an alignment mechanism according to claim 5, further comprising:

means for detecting that movement of the examining means by said second moving means reaches a limit; and means for informing, when the limit detecting means detects the examining means is at the limit, a direction in which said first moving means must be moved to displace the examining means from the limit.

7. An ophthalmic apparatus provided with an alignment mechanism according to claim 5, wherein the second moving means comprises driving means for moving the examining means in at least a lateral and a vertical directions.

8. An ophthalmic apparatus provided with an alignment mechanism according to claim 5, further comprising means for observing an image of an anterior part of the eye to be examined and means for forming indexes so as to superimpose on the image of the anterior part of the eye under observation through said observing means, thereby to inform a direction in which the examining means must be moved by said first moving means.

9. An ophthalmic apparatus provided with an alignment mechanism according to claim 5, further comprising means for returning said examining means to a basic position of said second moving means.

10. An ophthalmic apparatus comprising an examining means for examining an eye, wherein said examining means is operated after aligned at a predetermined position with respect to the eye to be examined, the apparatus comprising:

first means for moving said examining means in accordance with operation by an examiner with respect to the eye to be examined;

means for forming alignment indexes on the eye to be examined;

means for detecting the alignment indexes formed on the eye;

means for judging whether or not the alignment indexes detected by the index detecting means are within a predetermined area of the eye with respect to said examining means;

second means for further moving said examining means;

means for controlling, when the judging means judges that the alignment indexes are within a predetermined area, said second moving means to perform alignment based on results from said index detecting means; and means for returning said examining means to a basic position of said second moving means;

wherein said returning means comprises right and left eye detecting means for detecting whether the eye to be examined is a right eye or a left eye, and means for controlling said second moving means to move to the basic position when said right and left eye detecting means detects a change from one eye to another eye of the examinee.

11. An ophthalmic apparatus comprising an examining means for examining an eye, wherein said examining means is operated after aligned at a predetermined position with respect to the eye to be examined, the apparatus comprising:

first means for moving said examining means in accordance with operation by an examiner with respect to the eye to be examined;

means for forming alignment indexes on the eye to be examined;

means for detecting the alignment indexes formed on the eye;

means for judging whether or not the alignment indexes detected by the index detecting means are within a predetermined area of the eye with respect to said examining means;

second means for further moving said examining means;

means for controlling, when the judging means judges that the alignment indexes are within a predetermined area, said second moving means to perform alignment based on results from said index detecting means; and means for returning said examining means to a basic position of said second moving means;

wherein said returning means comprises measurement completion means for detecting a completion of measurement of the eye to be examined, and means for controlling said second moving means to move the examining means to the basic position when the measurement completion detecting means detects a completion of measurement of the eye to be examined.

12. An ophthalmic apparatus comprising an examining means for examining an eye, wherein said examining means is operated after aligned at a predetermined position with respect to the eye to be examined, the apparatus comprising:

first means for moving said examining means in accordance with operation by an examiner with respect to the eye to be examined;

means for forming alignment indexes on the eye to be examined;

means for detecting the alignment indexes formed on the eye;

means for judging whether or not the alignment indexes detected by the index detecting means are within a predetermined area of the eye with respect to said examining means;

second means for further moving said examining means;

means for controlling, when the judging means judges that the alignment indexes are within a predetermined area, said second moving means to perform alignment based on results from said index detecting means; and means for returning said examining means to a basic position of said second moving means;

wherein said returning means comprises input means for inputting a signal to perform alignment again with respect to the eye to be examined, and means for controlling the second moving means to move the examining means to the basic position based on the signal input by said input means.

13. An ophthalmic apparatus provided with an alignment mechanism according to claim 12, wherein said input means comprises means for detecting movement of said examining means toward the examiner's side by said first moving means.

14. An ophthalmic apparatus comprising an examining means for examining an eye, wherein said examining means is operated after aligned at a predetermined position with respect to the eye to be examined, the apparatus comprising:

first means for moving said examining means in accordance with operation by an examiner with respect to the eye to be examined;

means for irradiating alignment lights onto a cornea of the eye to be examined to form alignment indexes formed by the reflection of the alignment lights from the surface of the cornea;

means for detecting a position of the alignment indexes formed on the eye;

second means for further moving said examining means;

means for judging whether or not said examining means is within a predetermined rough alignment area, where said second moving means starts to move, with respect to the eye based on results from said index detecting means;

means for controlling said second moving means to perform alignment, when said judging means judges that said examining means is within the predetermined rough alignment area;

right and left eye detecting means for detecting whether the eye to be examined is a right eye or left eye; and means for controlling said second moving means to move to the basic position when said right and left eye detecting means detects a change from one eye to another eye of the examinee.

* * * * *